US00PP27107P2

(12) United States Plant Patent
McWhinnie et al.

(10) Patent No.: US PP27,107 P2
(45) Date of Patent: Aug. 30, 2016

(54) ***PHOTINIA* PLANT NAMED 'MCLARLOU'**

(50) Latin Name: *Photinia×fraseri*
Varietal Denomination: McLARLOU

(71) Applicants: Louise McWhinnie, Glascow (GB); Robert McLaren, Glascow (GB); Debbie McIsaac, Glascow (GB)

(72) Inventors: Louise McWhinnie, Glascow (GB); Robert McLaren, Glascow (GB); Debbie McIsaac, Glascow (GB)

(73) Assignee: McLARENS NURSERIES, Glasgow (GB)

( * ) Notice: Subject to any disclaimer, the term of this patent is extended or adjusted under 35 U.S.C. 154(b) by 136 days.

(21) Appl. No.: 14/120,617

(22) Filed: Jun. 10, 2014

(51) Int. Cl.
*A01H 5/12* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Penny J. Aguirre

(57) ABSTRACT

A new cultivar of *Photinia*, 'McLARLOU', characterized by its an evenly bushy, upright plant habit with short internode lengths between branches, its young leaves that emerge ruby red and pink in color, transitioning to tri-colored green, pink, and ruby red in color and finally maturing to olive green with a white margin, and its exhibits densely branched stems that are held at a narrow angle.

2 Drawing Sheets

Botanical classification: *Photinia×fraseri.*

Variety denomination: 'McLARLOU'.

BACKGROUND OF THE INVENTION

The present invention relates to a new and distinct cultivar of *Photinia×fraseri*, and will be referred to hereafter by its cultivar name, 'McLARLOU'. 'McLARLOU' is a new cultivar of an evergreen shrub for use as a landscape plant.

The Inventors discovered the new cultivar in summer of 2008 as a naturally occurring branch mutation of *Photinia* 'Red Robin' (not patented) in a production block at the Inventor's nursery in Glasgow, Scotland.

Asexual reproduction of the new cultivar was first accomplished using semi-hardwood stem cuttings by the Inventors in Glasgow, Scotland in 2008. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'McLARLOU' as unique cultivar of *Photinia.*

1. 'McLARLOU' exhibits an evenly bushy, upright plant habit with short internode lengths between branches.
2. 'McLARLOU' exhibits young leaves that emerge ruby red and pink in color, transitioning to tri-colored green, pink, and ruby red in color and finally maturing to olive green with a white margin.
3. 'McLARLOU' exhibits densely branched stems that are held at a narrow angle.

'Red Robin', the parent of 'McLARLOU', differs from 'McLARLOU' in having leaves that are persistently green in color. 'McLARLOU' can also be most closely compared to the *Photinia* cultivar 'Cassini' (U.S. Plant Pat. No. 15,160). 'Cassini' differs from 'McLARLOU' in having leaves apices that are more narrow in shape, in having branched stems held at a wider angle, in having longer internodes, in having a more open, less consistent in shape plant habit, and in having young foliage with leaf centers that are less red.

BRIEF DESCRIPTION OF THE DRAWINGS

The accompanying colored photographs illustrate the overall appearance and distinct characteristics of 2 year-old plants of the new *Photinia* as grown outdoors in 25-cm containers in Cambridge, United Kingdom.

The photograph is FIG. 1 provides a view of the overall habit of 'McLARLOU'.

Figure 1:
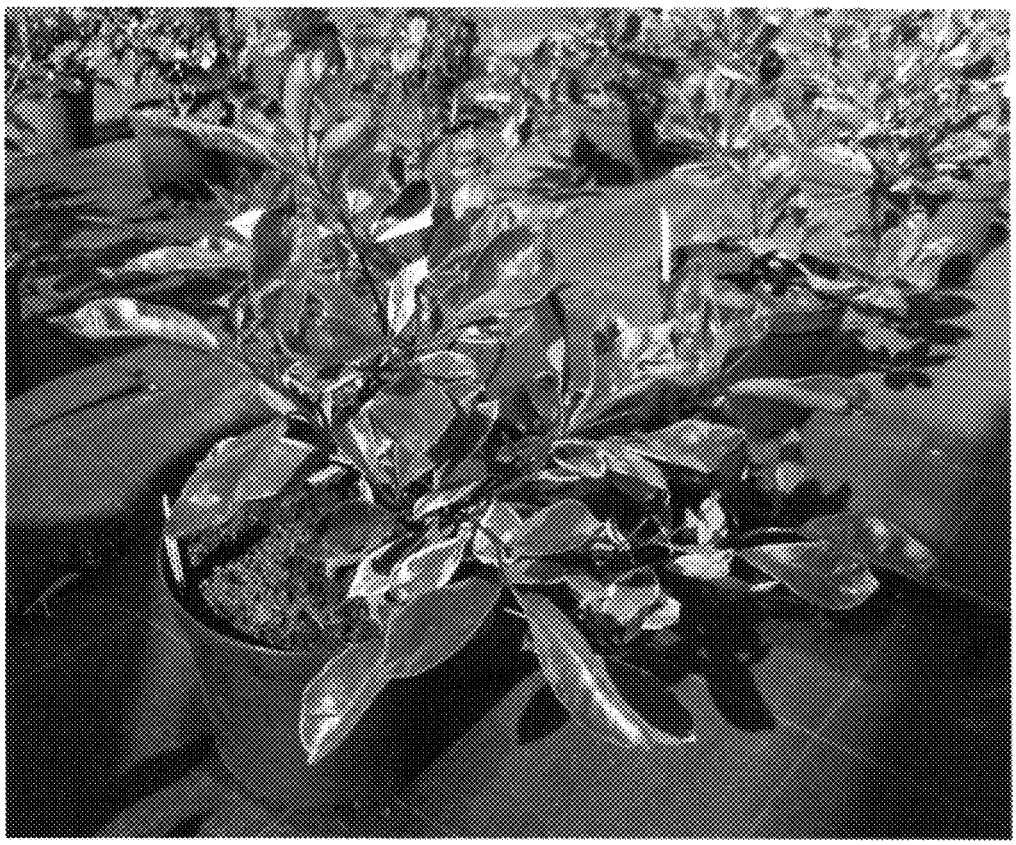
Figure 2:
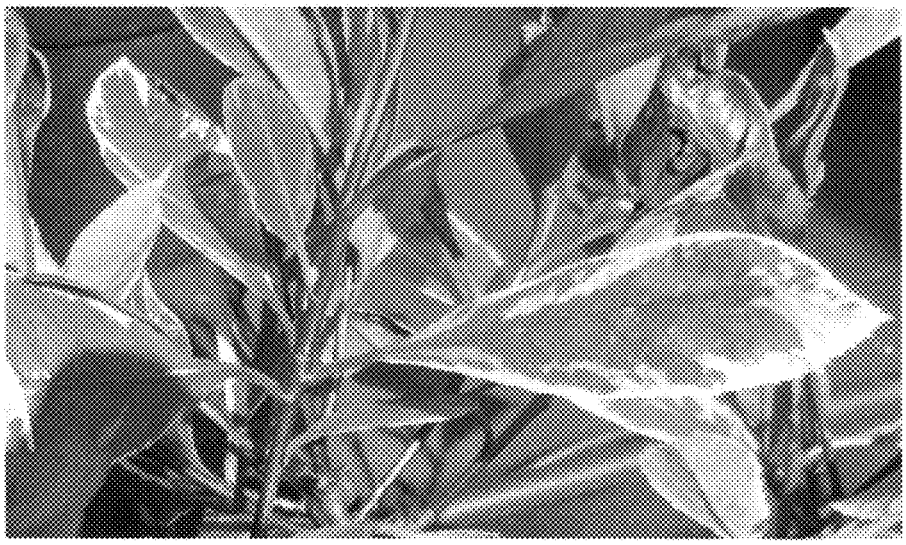
Figure 3:
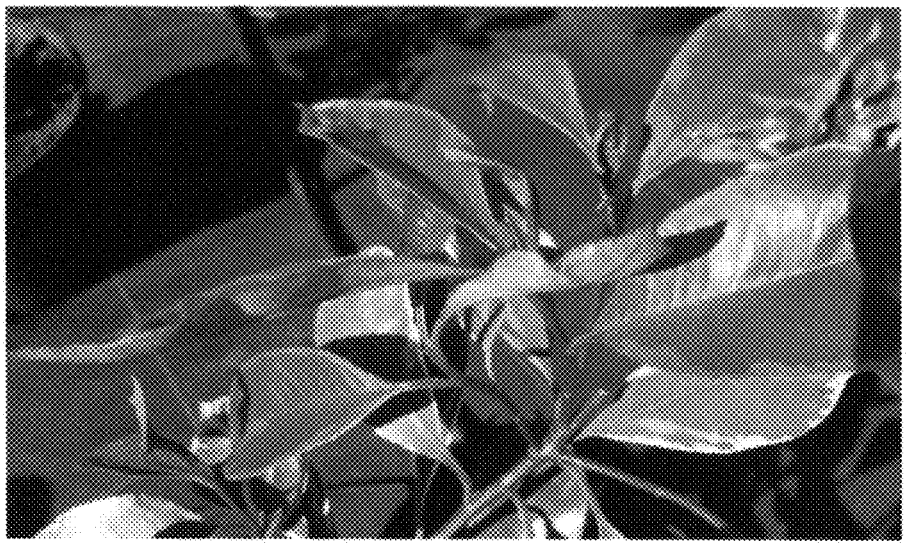

The photograph in FIG. 2 provides a close-up view of young and mature foliage of 'McLARLOU' and the photograph in FIG. 3 provides a close-up view of the maturing foliage of 'McLARLOU'.

The colors in the photographs are as close as possible with the digital photography techniques available and the color values cited in the detailed botanical description most accurately describe the colors of the new *Photinia.*

DETAILED BOTANICAL DESCRIPTION

The following is a detailed description of two year-old plants of the new *Photinia* as grown outdoors in 25-cm containers in Glasgow, Scotland. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen, perennial bushy shrub.

*Plant habit*.—Bushy and upright, narrow branch angles, consistent in plant shape.

*Height and spread*.—Reaches 1 to 1.25 m in height and 60 cm in spread in 3 years in the landscape.

*Cold hardiness*.—At least to U.S.D.A. Zone 8.

*Diseases and pests*.—No susceptibility or resistance to diseases or pests has been observed.

*Rooting habit*.—Fibrous, fine and dense.

*Propagation*.—Semi hardwood stem cuttings.

*Root development*.—Roots initiate in about 30 days in summer and fully develop as a young plant in about 2 months.

*Growth rate*.—Moderate.

Stem description:

*Shape*.—Rounded.

*Stem color*.—New twigs; 187C, mature bark; 178A to 178B.

*Stem size*.—Main branches; an average of 50 cm in length and 4 mm in width, lateral branches an average 25 cm in length and an average of 4 mm in diameter.

*Stem surface*.—Glabrous.

*Branching*.—Freely branched, an average of 7 lateral branches per main branch (as grown in a 25-cm container), medium in strength.

*Branch angle*.—An average of 30 degrees to vertical.

*Branch internode length*.—Average of 2 cm.

Foliage description:

*Leaf shape*.—Broad elliptic, elliptic, to narrow obovate.

*Leaf division*.—Simple.

*Leaf base*.—Cuneate.

*Leaf apex*.—Acuminate.

*Leaf fragrance*.—None.

*Leaf venation*.—Pinnate, color; identical to leaf.

*Leaf margins*.—Sharply serrate.

*Leaf arrangement*.—Alternate.

*Leaf attachment*.—Petiolate.

*Leaf surface*.—Upper and lower surface; glabrous and glossy.

*Leaf size*.—Average of 13 cm in length and 5.5 cm in width when mature with young leaves an average of 9 cm in length and 3 cm in width.

*Leaf internode length*.—Average of 2.3 cm.

*Leaf color*.—Newly expanded leaves upper surface; 183A with very narrow margin 185C turning to 200C with narrow irregular margin and patches 53D, maturing to N137C with small irregular patches of 188B and narrow irregular margin 58C to 58D, mature leaves upper surface; 188B with irregular margin 11D; newly expanded leaves lower surface; 183C, turning to 196B to 196D suffused with 50C to 50D throughout, maturing to 143C to 143D with very narrow margin 49C, mature leaves lower surface; 138D with margin 11D.

*Petioles*.—Average of 1.2 cm in length and 2.3 mm in width, 183A in color, surface is glabrous and glossy.

*Stipules*.—None observed.

Flower description: Flowering has not been observed since the date of discovery.

It is claimed:

1. A new and distinct cultivar of *Photinia* plant named 'McLARLOU', as herein illustrated and described.

* * * * *